Feb. 11, 1975 C. G. KLEHM Plant Pat. 3,683
PEONY PLANT
Filed Oct. 24, 1973
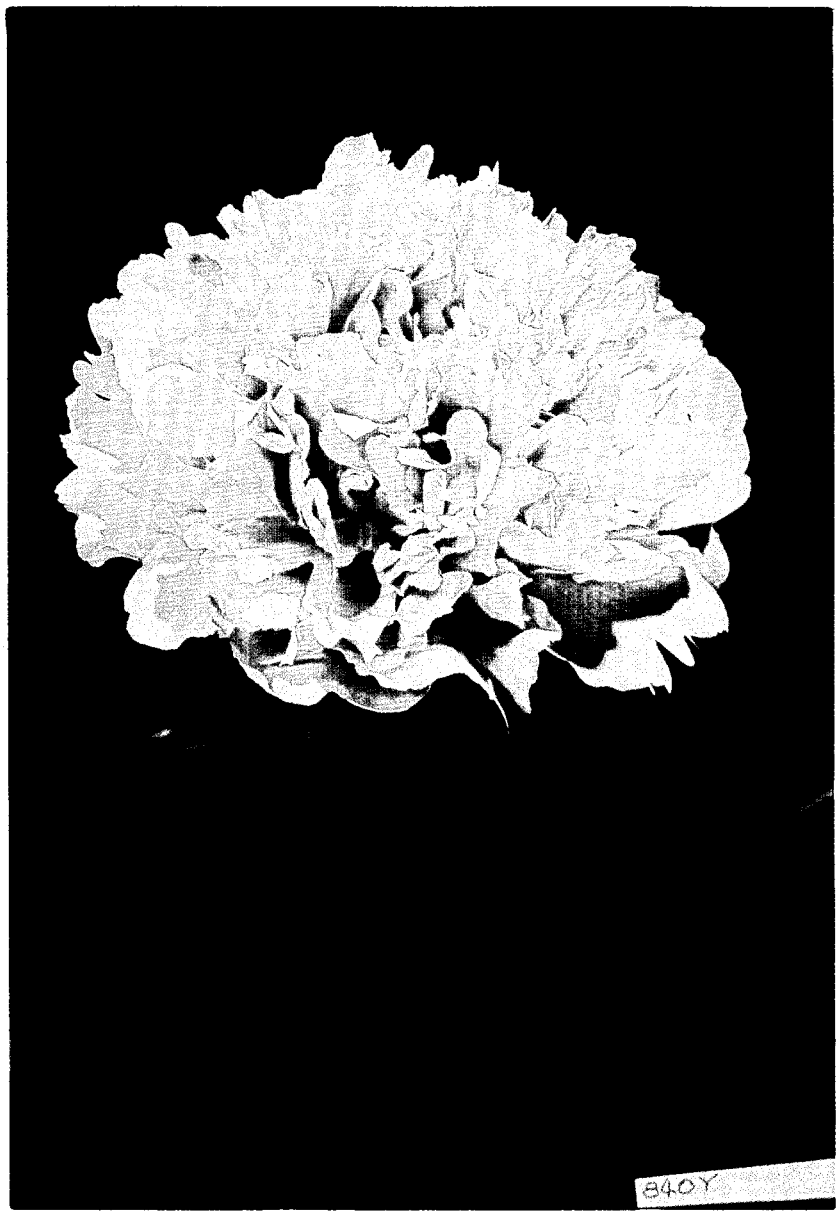

United States Patent

Plant Pat. 3,683
Patented Feb. 11, 1975

3,683
PEONY PLANT

Carl George Klehm, Arlington Heights, Ill., assignor to Klehm Properties, Inc., Arlington Heights, Ill.

Filed Oct. 24, 1973, Ser. No. 409,174
Int. Cl. A01h *5/00*
U.S. Cl. Plt.—68 1 Claim

ABSTRACT OF THE DISCLOSURE

A new variety of *Paeonia lactiflora* distinguished by its profuse production of rose type, double, medium pink blooms of large size which are carried on strong heavy stems, the flower petals having a unique glossy silver edging on all petal margins.

BACKGROUND OF THE NEW PLANT

This new variety of peony plant originated as a seedling of Mons. Jules Elie (unpatented) × an unnamed and unpatented variety maintained with my breeding stock and identified in my breeding records as 71D, the cross having been made by me in my breeding grounds at Arlington Heights, Ill., in the course of breeding efforts which I have carried on for many years with the object of developing new and distinctive peony varieties. This seedling was selected for propagation because of the large size of its blooms and the unique pink and silver coloration of the petals and asexual propagation of this plant, by root divisions, carried on under my direction at Arlington Heights, Ill., has demonstrated that its distinctive characteristics of flower size and coloring are firmly fixed and hold true from generation to generation. Propagation of this new variety by root division and on a commercial scale is now being done at production farms at Barrington, Ill., Champaign, Ill., and Arlington Heights, Ill.

DESCRIPTION OF THE DRAWING

My new variety of peony plant is illustrated by the accompanying photographic drawing which shows the form of the blossom in full bloom. The pink color rendition is as close as it is reasonably possible to obtain by conventional photographic procedures and the true color is shown by the color swatch affixed to the drawing immediately below the photographic view.

DESCRIPTION OF THE PLANT

The following is a detailed description of the new variety of peony plant with color specification according to the R.H.S. Colour Chart of The Royal Horticultural Society at London, England.

The plant

Origin: Seedling.
Parentage:
*Seed parent.*—Mons. Jules Elie (unpatented).

*Pollen parent.*—71D (unnamed and unpatented).
Classification: *Paeonia lactiflora.*
Form: Bush. Shape: Round.
Height: 36 to 38 inches.
Growth: Upright with strong stems of above average size, normally about ½ inch in diameter.
Foliage: Quantity—Abundant with 7 to 9 leaves per stem.
*Shape of leaf.*—Elliptically acute with smooth margin.
*Size of leaf.*—10 to 11 inches long.
*Aspect.*—Glossy.
*Leaflets.*—3 in number, 5 to 6 inches long.
*Petioles.*—2 to 2½ inches long.
*Ribs and veins.*—Pronounced.
*Rachis.*—1 to 2 inches.

The bud

Size: Medium. Diameter: 1½ inches. Depth: 1½ inches.
Form: Ovoid.

The flower

Blooming habit: Once annually, blooming profusely early in the season.
Size: Very large. Diameter 8 to 8½ inches.
Shape: Cup shaped when bloom first opens, becoming an extremely large rose shaped form of flower with a rather low crown.
Petalage: Form—Rose shape with slightly serrate or incised margins.
Color:
*Outer petals*—Red Purple 68B edged with silver.
*Inner petals*—Pinky Red, closest color 68B, edged with silver.
Fragance: Very mild.
Appearance: Satiny
Reproductive organs: None My new variety of peony plant is particularly distinguished by the large size of its blooms and its unique pink coloration with silver edging on all of the flower petals. This silver edging can be particularly pronounced in the years when the plants are exposed to more ultraviolet rays from the sun.

I claim:

1. A new and distinct variety of peony plant substantially as herein shown and described, characterized by the very large size of its full, rose type, double blossoms and the silver edging of the pale pink coloration of the blossom petals.

References Cited

UNITED STATES PATENTS

P.P. 3,264 12/1972 Klehm ---------- Plants—68
P.P. 3,271 12/1972 Klehm ---------- Plants—68

ROBERT E. BAGWILL, Primary Examiner